United States Patent
Cai et al.

(10) Patent No.: US 6,620,782 B1
(45) Date of Patent: Sep. 16, 2003

(54) SUBSTITUTED 2-AMINOBENZAMIDE CASPASE INHIBITORS AND THE USE THEREOF

(75) Inventors: Sui Xiong Cai, San Diego, CA (US); Yan Wang, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/527,225

(22) Filed: Mar. 16, 2000

Related U.S. Application Data

(60) Provisional application No. 60/158,386, filed on Oct. 12, 1999, and provisional application No. 60/124,675, filed on Mar. 16, 1999.

(51) Int. Cl.$^7$ .................. A61K 38/05; A01N 37/12; C07C 229/00; C12N 5/00
(52) U.S. Cl. .................. 514/10; 514/2; 514/9; 514/11; 514/538; 514/561; 514/560; 514/38; 514/41; 514/435; 514/254.1; 514/325; 514/410
(58) Field of Search .............. 514/10, 2, 9, 11, 514/538, 501, 561, 811, 824, 863, 866, 886, 894, 917; 560/38, 41; 435/41, 325, 254.1, 410

(56) References Cited

U.S. PATENT DOCUMENTS

| | | | |
|---|---|---|---|
| 4,153,688 A | | 5/1979 | Domicoli et al. .......... 424/177 |
| 4,518,528 A | | 5/1985 | Rasnick ................ 260/112.5 |
| 5,221,607 A | * | 6/1993 | Cordell et al. .............. 435/6 |
| 5,252,463 A | * | 10/1993 | Nelson et al. .............. 514/2 |
| 5,416,013 A | | 5/1995 | Black et al. .............. 435/226 |
| 5,430,128 A | | 7/1995 | Chapman et al. ......... 530/330 |
| 5,434,248 A | | 7/1995 | Chapman et al. ......... 530/330 |
| 5,462,939 A | | 10/1995 | Dolle et al. ............ 514/231.5 |
| 5,585,357 A | | 12/1996 | Dolle et al. ............... 514/18 |
| 5,677,283 A | | 10/1997 | Dolle et al. ............... 514/18 |
| 5,756,465 A | | 5/1998 | Sleath et al. .............. 514/17 |
| 5,843,904 A | | 12/1998 | Bemis et al. .............. 514/18 |
| 5,866,545 A | | 2/1999 | Hagmann et al. .......... 514/18 |
| 5,869,519 A | | 2/1999 | Karanewsky et al. ...... 514/415 |
| 5,932,549 A | | 8/1999 | Allen et al. ............... 514/18 |
| 6,153,591 A | | 11/2000 | Cai et al. .................. 514/19 |
| 6,184,210 B1 | * | 2/2001 | Keana et al. ............... 514/19 |
| 6,201,118 B1 | * | 3/2001 | Robidoux et al. ......... 540/500 |
| 6,355,618 B1 | * | 3/2002 | Cai et al. .................. 514/19 |
| 6,495,522 B1 | * | 12/2002 | Wang et al. ............... 514/19 |

FOREIGN PATENT DOCUMENTS

| | | |
|---|---|---|
| EP | 0 519 748 A2 | 12/1992 |
| EP | 0 618 223 A2 | 10/1994 |
| WO | WO 95/05071 | 3/1993 |
| WO | WO 96/03982 | 2/1996 |
| WO | WO 96/20721 | 7/1996 |
| WO | WO 96/33209 A1 | 10/1996 |
| WO | WO 98/10778 | 3/1998 |
| WO | WO 98/11109 | 3/1998 |
| WO | WO 98/41232 | 9/1998 |
| WO | WO 99/18781 | 4/1999 |
| WO | WO 99/47154 | 9/1999 |
| WO | WO 00/61542 | * 10/2000 |
| WO | WO 01/10383 A2 | 2/2001 |

OTHER PUBLICATIONS

Carrol Ezzel, Scientific America, pp. 152–153, Mar. 7, 1993.*

Varon et al., Dev. Neurosci., vol. 6, pp. 73–100, 1983/1984.*

Alnemri, E.S. et al., "Human ICE/CED–3 Protease Nomenclature," *Cell* 87:171, Cell Press, Cambridge, MA (1996).

An, S. and Knox, K.A., "Ligation of CD40 rescues Ramos–Burkitt lymphoma B Cells from calcium ionophore—and antigen receptor–triggered apoptosis by inhibiting activation of the cysteine protease CPP32/Yama and cleavage of its substrate PARP," *FEBS Lett.* 386:115–122, Elsevier Science Publishers B.V., Amsterdam (1996).

Angliker, H. et al., "The synthesis of lysylfluoromethanes and their properties as inhibitors of trypsin, plasmin and cathespin B," *Biochem J.* 241:871–875, The Biochemical Society, London, England (1987).

Black, R.A. et al., A Pre–aspartate–specific Protease from Human Leukocytes That Cleaves Pro–interleukin–1β, *J. Biol. Chem.* 264:5323–5326, The American Society for Biochemistry and Molecular Biology, Baltimore, MD (1989).

Black, S.C. et al., "Co–localization of the Cysteine Protease Caspase–3 with Apoptotic Myocytes after In Vivo Myocardial Ischemia and Reperfusion in the Rat," *J. Mol. Cell. Cardiol.* 30:733–742, Academic Press, Inc., New York, NY (Apr. 1998).

(List continued on next page.)

Primary Examiner—Christopher S. F. Low
Assistant Examiner—Abdel A. Mohamed
(74) Attorney, Agent, or Firm—Sterne, Kessler, Goldstein & Fox P.L.L.C.

(57) ABSTRACT

The present invention is directed to novel 2-aminobenzamide thereof, represented by the general Formula I:

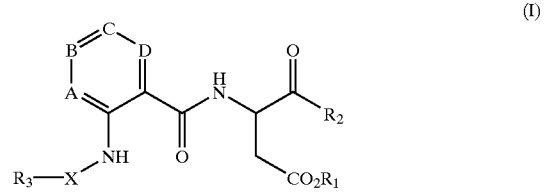

where $R^1$–$R_3$, X, and A—D are defined herein. The present invention also relates to the discovery that compounds having Formula I are potent inhibitors of caspases and apoptotic cell death. Therefore, the inhibitors of this invention can retard or block cell death in a variety of clinical conditions in which the loss of cells, tissues or entire organs occurs.

16 Claims, No Drawings

OTHER PUBLICATIONS

Bourne, E.J. et al., "Studies of Trifluoroacetic Acid. Part XVIII. Reaction of N–Aroylglycines with Perfluoro–carboxylic Anhydrides." *J. Chem. Soc. Part II*:1771–1775, The Chemical Society, London, England (1961).

Conaldi, P.G. et al., "HIV–1 Kills Renal Tubular Epithelial Cells In Vitro by Triggering an Apoptotic Pathway Involving Caspase Activation and Fas Upregulation," *J. Clin. Invest.* 102:2041–2049, The American Society for Clinical Investigation, Inc., New York, NY (Dec. 1998).

del Pozzo, O., and Lam, E., "Caspases and programmed cell death in the hypersensitive response of plants to pathogens," *Curr. Biol.* 8:1129–1132, Current Biology Ltd., London, England (Oct. 1998).

di Giovine, F.S., and Duff, G.W., "Interleukin 1: the first interleukin," *Immunology Today* 11:13–14, Elsevier Science Publishers Ltd., Barking, England (1990).

Dinarello, C. A., "Interleukin–1 and Interleukin–1 Antagonism," *Blood* 77:1627–1652, American Society for Hematology, Philadelphia, PA (1991).

Dolle, R.E. et al., "$P_1$ Aspartate–Based Peptide α–((2, 6–Dichlorobenzoyl)oxy)methyl Ketones as Potent Time–Dependent Inhibitors of Interleukin–1β–Converting Enzyme," *J. Med. Chem.* 37:563–564, American Chemical Society, Washington, DC (1994).

Dolle, R.E. et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme-Peptide Inhibitor Binding," *J. Med. Chem.* 37:3863–3866, American Chemical Society, Washington, DC (1994).

Dolle, R.E. et al., "Aspartyl α–((Diphenylphosphiny-l)oxy)methyl Ketones as Novel Inhibitors of Interleukin–1β Converting Enzyme. Utility of the Diphenylphosphinic Acid Leaving Group for the Inhibition of Cysteine Proteases," *J. Med. Chem.* 38:220–222, American Chemical Society, Washington, DC (1995).

Ellis, R.E. et al., "Mechanisms and Functions of Cell Death," *Ann. Rev. Cell Bio.* 7:663–698, Annual Reviews, Palo Alto, CA (1991).

Emery, E. et al., "Apoptosis after traumatic human spinal cord injury," *J. Neurosurg.* 89:911–920, American Association of Neurological Surgeons, Charlottesville, VA (Dec. 1998).

Goldberg, Y.P. et al., "Cleavage of huntingtin by apopain, a proapoptotic cysteine protease, is modulated by the polyglutamine tract," *Nature Genetics* 13:442–449, Nature Publishing Co., New York, NY (1996).

Graybill, T.L. et al., "α–((Tetronoyl)oxy)—and α–((Tetramoyl)oxy)methyl Ketone Inhibitors of the Interleukin–1α Converting Enzyme (Ice)," *Bioorg. Med. Chem. Lett.* 7:41–46, Elsevier Science Ltd., Oxford, England (1997).

Greenberg, J.T. et al., "Programmed Cell Death in Plants: A Pathogen–Triggered Response Activated Coordinately with Multiple Defense Functions," *Cell* 77:551–563, Cell Press, Cambridge, MA (1994).

Grobmyer, S.R. et al., "Peptidomimetic Fluoromethylketone Rescues Mice from Lethal Endototoxic Shock," *Mol. Med.* 5:585–594, Johns Hopkins University Press, Baltimore, MD (Sep. 1999).

Hara, H. et al., "Inhibition of interleukin 1β converting enzyme family proteases reduces ischemic and excitotoxic neuronal damage," *Proc. Natl. Acad. Sci. USA* 94:2007–2012, National Academy of Sciences, Washington, DC (Mar. 1997).

Hiraoka, J. et al., "Participation of apoptosis in renal amyloidosis," *Jpn. J. Nephrol.* 40:276–283, Japanese Society of Nephrology, Tokyo, Japan (May 1998).

Hotchkiss, R.S. et al., "Prevention of lymphocyte cell death in sepsis improves survival in mice," *Proc. Natl. Acad. Sci. USA* 96:14541–14546, National Academy of Sciences, Washington, DC (Dec. 1999).

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immun.* 160:3480–3486, American Association of Immunologists, Baltimore, MD (Apr. 1998).

Jones, R.A. et al., "Fas–Mediated Apoptosis in Mouse Hepatocytes Involves the Processing and Activation of Caspases," *Hepatology* 27:1632–1642, American Association for the Study of Liver Diseases, Philadelphia, PA (Jun. 1998).

Kermer, P. et al., "Inhibition of CPP32–Like Proteases Rescues Axotomized Retinal Ganglion Cells from Secondary Cell Death In Vivo," *J. Neuroscience* 18:4656–4662, Society for Neuroscience, Washington, DC (Jun. 1998).

Kubo, S. et al., "Hepatocyte injury in tyrosinemia type 1 is induced by fumarylacetoacetate and is inhibited by caspase inhibitors," *Proc. Natl. Acad. Sci. USA* 95:9552–9557, National Academy of Sciences, Washington, DC (Aug. 1998).

Lepschy, J., "Acylierung von Oxazolinonen–(5) unter besonderer Berücksichtigung der Dakin–West–Reaktion trifunktioneller Aminosäuren," *Ph.D. Thesis*, Technischen Universität München (1971).

Lieberthal, W. et al., "Necrosis and Apoptosis in Acute Renal Failure," *Sem. Nephr.* 18:505–518, W.B. Saunders Company, Philadelphia, PA (Sep. 1998).

Lotem, J. and Sachs, L., "Differential suppression by protease inhibitors and cytokines of apoptosis induced by wild–type p53 and cytotoxic agents," *Proc. Natl. Acad. Sci. USA* 93:12507–12512, National Academy of Sciences, Washington, DC (1996).

Mattson, M.P. et al., "Amyloid β–peptide induces apoptosis–related events in synapses and dendrites," *Brain Res.* 807:167–176, Elsevier Science B.V., Amsterdam, Netherlands (Oct. 1998).

Maulik, N. et al., "Oxidative stress developed during the reperfusion of ischemic myocardium induces apoptosis," *Free Rad. Biol. & Med.* 24:869–875, Elsevier Science Inc., Tarrytown, NY (Mar. 1998).

Miller, P.E. et al., "Photoreceptor cell death by apoptosis in dogs with sudden acquired retinal degeneration syndrome," *Am. J. Vet. Res.* 59:149–152, American Veterinary Medical Association, Schaumburg, IL (Feb. 1998).

Miura, M. et al., "Induction of Apoptosis in Fibroblasts by IL–1β–Converting Enzyme, a Mammalian Homolog of the C. elegans Cell Death Gene ced.3," *Cell* 75:653–660, Cell Press, Cambridge, MA (1993).

Mjalli, A.M.M. et al., "Phenylalkyl as Potent Reversible Inhibitors of Interleukin–1β Converting Enzyme," *Bioorg. Med. Chem. Lett.* 3:2689–2692.

Mjalli, A.M.M. et al., "Activated Ketones as Potent Reversible Inhibitors of Interleukin–1β Converting Enzyme," *Bioorg. Med. Chem. Lett.* 4:1965–1968, Elsevier Science Ltd., Oxford, England (1994).

Mjalli, A.M.M. et al., "Inhibition of Interleukin–1β Converting Enzyme by N–acyl–aspartic acid Ketones," *Bioorg. Med. Chem. Lett.* 5:1405–1408 Elsevier Science Ltd., Oxford, England (1995).

Mjalli, A.M.M. et al., "Inhibition of Interleukin–1β Converting Enzyme by N–acyl–aspartyl Aryloxymethyl Ketones," *Bioorg. Med. Chem Lett.* 5:1409–1414, Elsevier Science Ltd., Oxford, England (1995).

Mosley, B. et al., "The Interleukin–1 Receptor Binds the Human Interleukin–1α Precursor but Not the Interleukin–1β Precursor," *J. Biol. Chem.* 262:2941–2944, American Society for Biological Chemists, Inc., Baltimore, MD (1987).

Mundle, S. D. et al., "Evidence for Involvement of Tumor Necrosis Factor–α in Apoptotic Death of Bone Marrow Cells in Myelodysplastic Syndromes," *Am. J. Hemat.* 60:36–47, Wiley–Liss, Inc., New York, NY (Jan. 1999).

Oppenheim, J. J. et al., "There is more than one interleukin–1," *Immun. Today* 7:45–56, Elsevier Science Publishers B.V., Amsterdam, Netherlands (1986).

Orrenius, S., "Apoptosis: molecular mechanisms and implications for human disease," *J. Internal Medicine* 237:529–536, Blackwell Science Ltd., Oxford, England (1995).

Ortiz, A. et al., "Cyclosporine A induces apoptosis in murine tubular epithelial cells: Role of caspases." *Kidney Int'l.* 54:S–25–S–29, International Society of Nephrology, Amsterdam, Netherlands (Dec. 1998).

Peleg, S. et al., "1,25–Dihydroxyvitamin $D_3$ and its analog inhibit acute myelogenous leukemia progenitor proliferation by suppressing interleukin–1β production," *Chemical Abstracts 127*, Abstract No. 315124p, American Chemical Society, Washington, DC (1997).

Rasnick, D., "Synthesis of Peptide Fluoromethyl Ketones and the Inhibitors of Human Cathepsin B," *Anal. Biochem.* 149:461–465, Academic Press, New York, NY (1985).

Rauber, P. et al., "The synthesis of peptidylfluoromethanes and their properties as inhibitors of serine proteinase and cysteine proteinases," *Biochem J.* 239:633–640, The Biochemical Society, London, England (1986).

Revesz, L. et al., "Synthesis of P1 Aspartate–Based Peptide Acylomymethyl and Fluoromethyl Ketones as Inhibitors of Interleukin–1β–Converting Enzyme," *Tet. Lett.* 35:9693–9696, Elsevier Science Ltd., United Kingdom (1994).

Rich, D.H., "Inhibitors of aspartic proteinases," in *Proteinase inhibitors Research monographs in cell and tissue physiology.* vol. 12, Barrett, A.J. and G. Salvesen, eds., Elsevier, Amsterdam, Holland, pp. 179–208 (1986).

Richberg, M.H. et al., "Dead cells do tell tales," *Curr. Op. Plant Biol.* 1:480–485, Elsevier Science Ltd., United Kingdom (Dec. 1998).

Rodriguez, I. et al., "Systemic Injection of a Tripeptide Inhibits th Intracellular Activation of CPP32–like Proteases In Vivo and Fully Protects Mice against Fas–mediated Fulminant Liver Destruction and Death," *J. Exp. Med.* 184:2067–2072, The Rockefeller University Press, New York, NY (1996).

Shaw, E. et al., "Peptidyl fluoromethyl ketones as thiol protease inhibitors," *Biomed. Biochim. Acta* 45:1397–1403, Academic Verlag, Berlin, Germany (1986).

Semple, G. et al., "Peptidomimetic Aminomethylene Ketone Inhibitors of Interleukin–1β–Converting Enzyme (ICE)," *Bioorg. Med. Chem. Lett.* 8:959–964, Elsevier Science Ltd., Oxford, England (1998).

Sheikh, M.S. et al., "Ultraviolet–irradiation–induced apoptosis is mediated via ligand independent activation of tumor necrosis factor receptor 1," *Oncogene* 17:2555–2563, Stockton Press, London, England (Nov. 1998).

Sleath, P.R. et al., "Substrate Specificity of the Protease That Pocesses Human Intereukin–1β," *J. Bio. Chem.* 265:14526–14528, American Society for Biochemistry and Molecular Biology, Inc., Baltimore, MD (1990).

Slomiany, B.L. et al., "Activation of Apoptotic Caspase–3 and Nitric Oxide Synthase–2 in Buccal Mucosa with Chronic Alcohol Ingestion," *Biochem. & Mol. Bio. Int'l.* 45:1199–1209, Academic Press, Sydney, Australia (Sep. 1998).

Steinberg, D., "Caspase Inhibitors. Molecules Sought For Treatment of Diverse Disorders," *Gen. Eng. News* 18:16, 38,51, Mary Ann Liebert, Inc., New York, NY (Jul. 1998).

Suzuki, A., "The Dominant Role of CPP32 Subfamily in Fas–Mediated Hepatitis," *Proc. Soc. Exp. Biol. Med.* 217:450–454, Society for Experimental Biology and Medicine, Cambridge, MA (Apr. 1998).

Thornberry, N.A. et al., "A novel heterodimeric cysteine protease is required for interleukin–1β processing in monocytes," *Nature* 356:768–774, Nature Publishing Group, London, England (1992).

Thornberry, N.A. et al., "A Combinatorial Approach Defines Specificities of Members of the Caspase Family and Granzyme B," *J. Biol. Chem.* 272:17907–17911, American Society for Biochemistry and Molecular Biology, Inc., Baltimore, MD (1997).

Thornberry, N.A., "Caspases: key mediators of apoptosis," *Chem. Biol.* 5:R97–R103, Current Biology Ltd., London, England (May 1998).

Thornberry, N.A. et al., "Inactivation of Interleukin–1β Converting Enzyme by Peptide (Acyloxy)methyl Ketones," *Biochemistry* 33:3934–3940, American Chemical Society, Washington, DC (1994).

Wataya, Y. et al., "Cytotoxic mechanism of 1–(3–C–ethynyl–β–D–ribo–pentofuranosyl)cytosine (ECyd)," *Chemical Abstracts* 132, Abstract No. 273983p, American Chemical Society, Washington, DC (May 2000).

Weil, M. et al., "Is programmed cell death required for neural tube closure?" *Curr. Biol.* 7:281–284, Current Biology Ltd., London, England (Apr. 1997).

Wyllie, A.H. et al., "Cell Death: The Significance of Apoptosis," *Int. Rev. Cyt.* 68:251–306, Academic Press, Inc., New York, NY (1980).

Wyllie, A.H., "Cell death: a new classification separating apoptosis from necrosis," in *Cell Death in Biology and Pathology*, Bowen and Lockin, eds., Chapman and Hall, New York, NY, pp. 9–34 (1981).

Xue, D. et al., "The Time Course for Infarction in a Rat Model of Transient Focal Ischemia," *Stroke* 21:166, Abstract No. 36, American Heart Association, Baltimore, MD (1990).

Yuan, J. et al., "The *C. elegans* Cell Death Gene ced–3 Encodes a Protein Similar to Mammalian Interleukin–1β–Converting Enzyme," *Cell* 75:641–652, Cell Press, Inc., Cambridge, MA (1993).

International Search Report for International Application No. PCT/US00/06398, mailed Aug. 28, 2000.

U.S. patent application Ser. No. 09/653,279, Keana et al., filed Aug. 30, 2000.

\* cited by examiner

SUBSTITUTED 2-AMINOBENZAMIDE CASPASE INHIBITORS AND THE USE THEREOF

CROSS-REFERENCE TO RELATED APPLICATIONS

The present application claims the benefit of the filing date of U.S. Provisional Application No. 60/158,386, filed Oct. 12, 1999, and U.S. Provisional Application No. 60/124,675, filed Mar. 16, 1999.

BACKGROUND OF THE INVENTION

1. Field of the Invention

This invention is in the field of medicinal chemistry. In particular, the invention relates to substituted 2-aminobenzamides and analogs that are inhibitors of caspases. The invention also relates to the use of these 2-aminobenzamides and analogs for reducing or treating apoptotic cell death and/or reducing interleukin 1-β production.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO 96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68:251 (1980); Ellis et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H. et. al. *Immunology Today*, 7, 45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. Interleukin-1β converting enzyme (ICE) is a protease responsible for the activation of interleukin-1β (IL-1β) (Thornberry, N. A., et al., *Nature* 356:768 (1992); Yuan, J., et al., *Cell* 75:641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and $ICE_{rel}III$. The proteolytic activity of this family of cysteine proteases, whose active site (a cysteine residue) is essential for ICE-mediated apoptosis, appears critical in mediating cell death (Miura et al., *Cell* 75:653–660 (1993)). This gene family has recently been named caspases (Alnernri, E. S. et. al. *Cell*, 87, 171 (1996), and Thornberry, N. A. et. al. *J. Biol. Chem.* 272, 17907–17911 (1997)) and divided into three groups according to its known functions. Table 1 summarizes these known caspases.

TABLE 1

| Enzyme* |
|---|
| Group I: mediators of inflammation |
| Caspase-1 (ICE) |
| Caspase-4 ($ICE_{rel}$-II, TX, ICH-2) |
| Caspase-5 ($ICE_{rel}$-III, TY) |
| Group II: effectors of apoptosis |
| Caspase-2 (ICH-1, mNEDD2) |
| Caspase-3 (apopain, CPP-32, YAMA) |
| Caspase-7 (Mch-3, ICE-LAP3, CMH-1) |
| Group III: activators of apoptosis |
| Caspase-6 (Mch2) |
| Caspase-8 (MACH, FLICE, Mch5) |
| Caspase-9 (ICE-LAP6, Mch6) |
| Caspase-10 |

IL-1 is also a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Immunology Today* 11:13 (1990)).

Many potent caspase inhibitors have been prepared based on the peptide substrate structures of caspases. However, in contrast to their potency in vitro, no inhibitors with good efficacy ($IC_{50}$<1 μM) in whole-cell models of apoptosis have been reported (Thornberry, N. A. *Chem. Biol.* 5:R97–103 (1998)). Therefore the need exists for cell death inhibitors that are efficacy in whole-cell models of apoptosis and active in animal model of apoptosis. These inhibitors thus can be employed as therapeutic agents to treat disease states in which regulated cell death and the cytokine activity of IL-1 play a role.

WO 93/05071 discloses peptide ICE inhibitors with the formula:

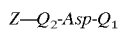

wherein Z is an N-terminal protecting group; $Q_2$ is 0 to 4 amino acids such that the sequence $Q_2$-Asp corresponds to at least a portion of the sequence Ala-Tyr-Val-His-Asp; $Q_1$ comprises an electronegative leaving group.

WO 96/03982 discloses aspartic acid analogs as ICE inhibitors with the formula:

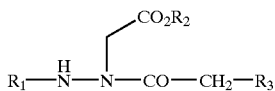

wherein $R_2$ is H or alkyl; $R_3$ is a leaving group such as halogen; $R_1$ is heteroaryl-CO or an amino acid residue.

U.S. Pat. No. 5,585,357 discloses peptidic ketones as ICE inhibitors with the formula:

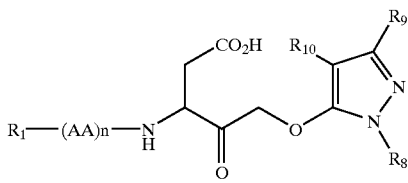

wherein n is 0–2; each AA is independently L-valine or L-alanine; $R_1$ is selected from the group consisting of N-benzyloxycarbonyl and other groups; $R_8$, $R_9$, $R_{10}$ are each independently hydrogen, lower alkyl and other groups.

Mjalli et al. (*Bioorg. Med. Chem. Lett.*, 3, 2689–2692, 1993) report the preparation of peptide phenylalkyl ketones as reversible inhibitors of ICE, such as:

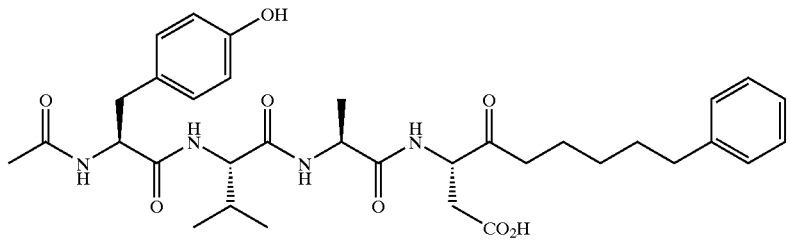

Thornberry et al. (*Biochemistry*, 33, 3934–3940, 1994) report the irreversible inactivation of ICE by peptide acyloxymethyl ketones:

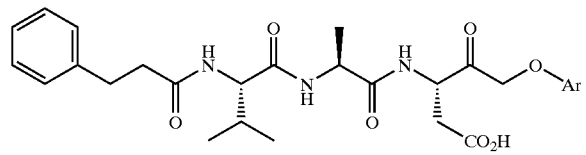

wherein Ar is COPh-2,6-(CF$_3$)$_2$, COPh-2,6-(CH$_3$)$_2$, Ph-F$_5$ and other groups.

Dolle et al. (*J. Med. Chem.* 37, 563–564, 1994) report the preparation of $P_1$ aspartate-based peptide α-((2,6-dichlorobenzoyl)oxy)methyl ketones as potent time-dependent inhibitors of ICE, such as:

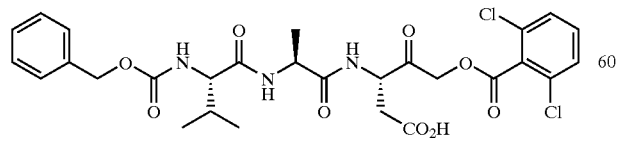

Mjalli et al. (*Bioorg. Med. Chem. Lett.*, 4, 1965–1968, 1994) report the preparation of activated ketones as potent reversible inhibitors of ICE:

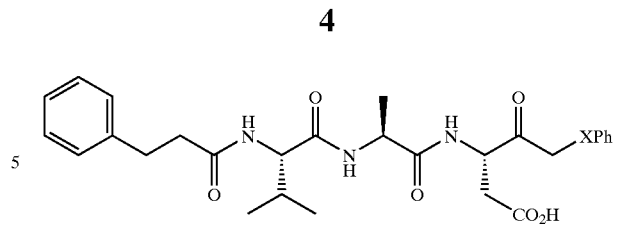

wherein X is NH(CH$_2$)$_2$, OCO(CH$_2$)$_2$, S(CH$_2$)$_3$ and other groups.

Dolle et al. (*J. Med. Chem.* 37, 3863–3866, 1994) report the preparation of α-((1-phenyl-3-(trifluoromethyl)-pyrazol-5-yl)oxy)methyl ketones as irreversible inhibitor of ICE, such as:

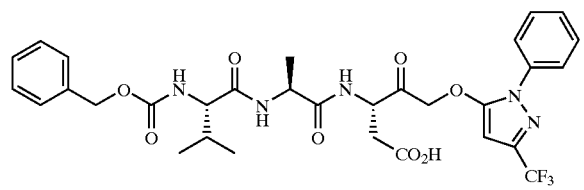

Mjalli et al. (*Bioorg Med. Chem. Lett.*, 5, 1405–1408, 1995) report inhibition of ICE by N-acyl-Aspartic acid ketones:

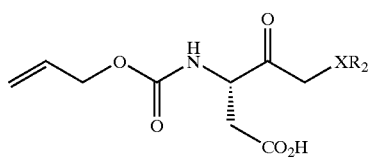

wherein XR$_2$ is NH(CH$_2$)$_2$Ph, OCO(CH$_2$)$_2$cyclohexyl and other groups.

Mjalli et al. (*Bioorg Med. Chem. Lett.*, 5, 1409–1414, 1995) report inhibition of ICE by N-acyl-aspartyl aryloxymethyl ketones, such as:

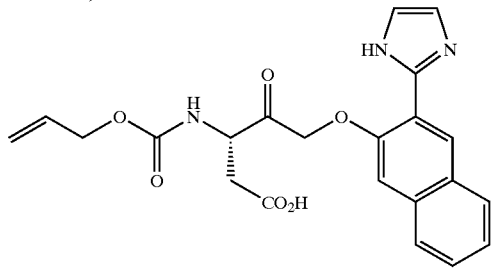

Dolle et al. (*J. Med. Chem.* 38, 220–222, 1995) report the preparation of aspartyl α-((diphenylphosphinyl)oxy)methyl ketones as irreversible inhibitors of ICE, such as:

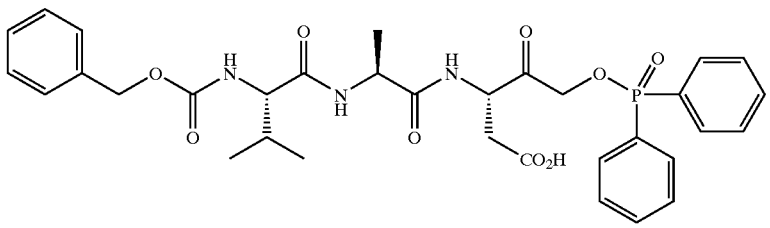

Graybill et al. (*Bioorg. Med. Chem. Lett.*, 7, 41–46, 1997) report the preparation of α-((tetronoyl)oxy)- and α-((tetramoyl)oxy)methyl ketones as inhibitors of ICE, such as:

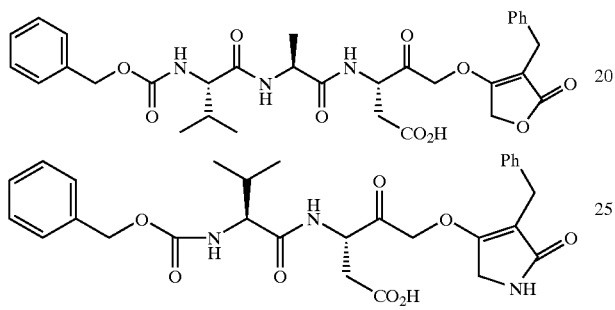

Semple et al. (*Bioorg. Med. Chem. Lett.*, 8, 959–964, 1998) report the preparation of peptidomimetic aminomethylene ketones as inhibitors of ICE, such as:

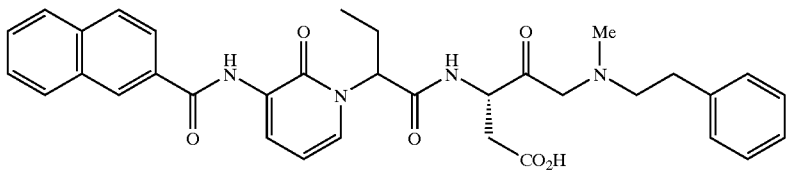

SUMMARY OF THE INVENTION

The invention relates to compound of Formulae I, II and III:

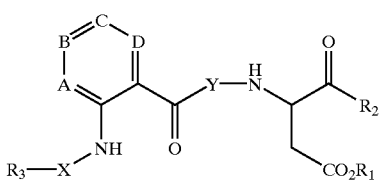

(I)

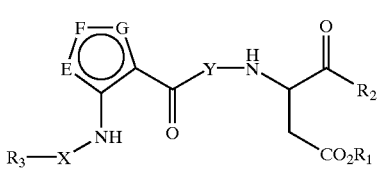

(II)

-continued (III)

(structure for formula III)

wherein $R_1$ is an optionally substituted alkyl or hydrogen;

$R_3$ is an N-protecting group;

$R_2$ is hydrogen or optionally substituted alkyl;

A is $CR_6$ or nitrogen;

B is $CR_7$ or nitrogen;

C is $CR_8$ or nitrogen;

D is $CR_9$ or nitrogen;

provided that not more than two of A, B, C or D is nitrogen; and $R_6$–$R_9$ independently are hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) $C_6$–$C_{10}$ aryl($C_2$–$C_6$) alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_6$ and $R_7$, or $R_1$ and $R_8$, or $R_8$ and $R_9$ are taken together with the carbon atoms to which they are attached to form a carbocycle or heterocycle;

E is $CR_{14}$, nitrogen, oxygen or sulfur;

F is $CR_{15}$, nitrogen, oxygen or sulfur;

G is $C_{16}$, nitrogen, oxygen or sulfur;

provided that only one of E, F, G is nitrogen, oxygen or sulfur; where $R_{14}$–$R_{16}$ are independently hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl ($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_{14}$ and $R_{15}$, or $R_{15}$ and $R_{16}$, are taken together with the carbon atoms to which they are attached to form a carbocycle or heterocycle;

Q represents an optionally substituted saturated or partially saturated carbocycle or heterocycle;

X is a peptide of 1–4 amino acids or a bond; and

Y is a peptide of 1–4 amino acids or a bond.

The invention relates to the discovery that the compounds represented by Formulae I, II and III are inhibitors of caspases. The invention also relates to the use of the compounds of the invention for reducing, preventing or treating maladies in which apoptotic cell death is either a causative factor or a result. Examples of uses for the present invention include protecting the nervous system following focal ischemia and global ischemia; treating neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; treating heart disease including myocardial infarction, congestive heart failure and cardiomyopathy; treating retinal disorders; treating autoimmune disorders including lupus erythematosus, rheumatoid arthritis, type I diabetes, Sjögren's syndrome and glomerulonephritis; treating polycystic kidney disease and anemia/erythropoiesis; treating immune system disorders, including AIDS and SCIDS; treating or ameliorating sepsis or multi-organ failure in an animal; reducing or preventing cell, tissue and organ damage during transplantation; reducing or preventing cell line death in industrial biotechnology; reducing or preventing alopecia (hair loss); reducing the premature death of skin cells; treating or ameliorating apoptotic cell death in acute pancreatitus; treating or preventing the inflammatory response in psoriasis or inflammatory bowel disease; and treating or ameliorating organ apoptosis after burn injury.

The present invention provides pharmaceutical compositions comprising a compound of Formulae I, II and III in an effective amount to reduce apoptotic cell death in an animal.

The present invention also provides preservation or storage solutions for mammalian organs or tissue, or growth media for mammalian or yeast cells, wherein an effective amount of a compound of Formula I, II and III is included in said solutions or media in order to reduce apoptotic cell death in said organs, tissue or cells.

The invention also relates to the use of caspase inhibitors for treating, ameliorating, and preventing non-cancer cell death during chemotherapy and radiation therapy and for treating and ameliorating the side effects of chemotherapy and radiation therapy of cancer.

In particular, the invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a caspase inhibitor.

Detailed Description of the Invention

The inhibitors of caspases and apoptotic cell death of the present invention are compounds having the general Formulae I, II and III:

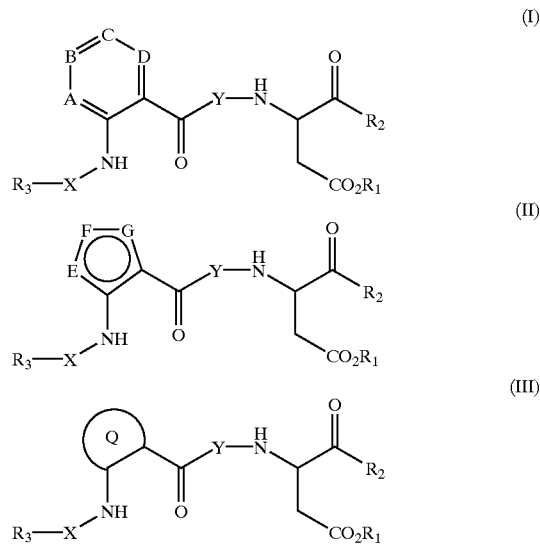

or pharmaceutically acceptable salts or prodrugs thereof, wherein:

$R_1$ is an optionally substituted alkyl or hydrogen;

$R_3$ is a N-protecting group including t-butyloxycarbonyl, acetyl, and benzyloxycarbonyl;

$R_2$ is hydrogen or optionally substituted alkyl;

A is $CR_6$ or nitrogen;

B is $CR_7$ or nitrogen;

C is $CR_8$ or nitrogen;

D is $CR_9$ or nitrogen; provided that not more than two of A, B, C or D is nitrogen; and $R_6$–$R_9$ independently are hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$) alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle;

E is $C_{14}$, nitrogen, oxygen or sulfur;

F is $C_{15}$, nitrogen, oxygen or sulfur;

G is $C_{16}$, nitrogen, oxygen or sulfur; provided that only one of E, F, G is nitrogen, oxygen or sulfur; where $R_{14}$–$R_{16}$ are independently hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) alkyl, $C_6$–$C_{10}$ aryl($C_2$–$C_6$)alkenyl, $C_6$–$C_{10}$ aryl($C_2$–$C_6$) alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_{14}$ and $R_{15}$, or $R_{15}$ and $R_{16}$ are taken together with the carbon atoms to which they are attached to form a carbocycle or heterocycle;

Q represents an optionally substituted saturated or partially saturated carbocycle or heterocycle;

X is a peptide of 1–4 amino acids or a bond; And

Y is a peptide of 1–4 amino acids or a bond. Where X or Y is one amino acid, it may be any one of the common 20 amino acids e.g., Ala, Val, Leu, Ile, Pro, Phe, Trp, Met, Gly, Ser, Thr, Cys, Tyr, Asp, Asn, Glu, Asn, Lys, Arg and His. Where X is a peptide, it may be Asp-Glu, Asp-Ala, Asp-Phe, Val-Glu, Leu-Glu, Thr-Glu, Ile-Glu, Tyr-Glu, Trp-Glu. Where Y is a peptide, it may be Glu-His, Glu-Ile, Glu-Thr, Glu-Val, Glu-Phe, Thr-His, Val-His, Ala-His and Glu-Pro.

With respect to $R_1$, preferred alkyl groups are $C_{1-6}$ alkyl groups, e.g. methyl, ethyl, propyl, isopropyl, isobutyl, pentyl and hexyl groups; and substituted $C_{1-6}$ alkyl groups, e.g. $CH_2OCH_3$ and $CH_2OCOCH_3$ (AM).

The invention relates to the discovery that the compounds represented by Formulae I, II and III are inhibitors of caspases. These inhibitors slow or block cell death in a variety of clinical conditions and industrial applications in which the loss of cells, tissues or entire organs occurs. Therefore, the invention is also related to methods of treating, preventing or reducing conditions in which apoptosis plays a role. These conditions are more fully described below.

The methods comprise administering to an animal in need of such treatment an inhibitor of the present invention, or a pharmaceutically acceptable salt or prodrug thereof, in an amount effective to inhibit apoptotic cell death.

Preferred embodiments of the compounds of Formulae I, II and III that may be employed as inhibitors of caspases are represented by Formula IV:

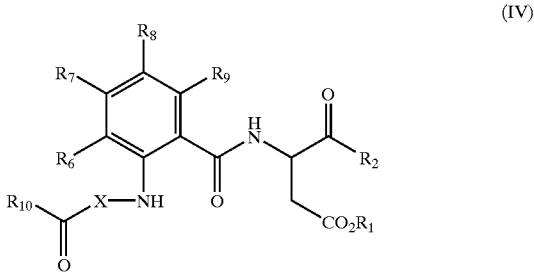

(IV)

or pharmaceutically acceptable salts or prodrugs thereof wherein $R_1$ $R_2$-, $R_6$–$R_9$ and X are as defined previously with respect to Formula I.

Examples of bridges formed by $R_6$ and $R_7$, or $R_7$ and $R_8$, or $R_8$ and $R_9$ taken together are —$OCH_2O$—, —$OCF_2O$—, —$(CH_2)_3$—, —$(CH_2)_4$—, —$OCH_2CH_2O$—, —$CH_2N(R_{13})$ $CH_2$—, —$CH_2CH_2N(R_{13})CH_2$—, —$CH_2N(R_{13})$ $CH_2CH_2$— and —CH=CH—CH=CH—; where $R_{13}$ is hydrogen, alkyl or cycloalkyl.

$R_{10}$ is hydrogen, $C_1$–$C_6$ alkoxy, $C_1$–$C_6$ alkyl, $C_1$–$C_6$ haloalkyl, $C_6$–$C_{10}$ aryl, $C_4$–$C_7$ cycloalkyl, $C_6$–$C_{10}$ aryl($C_1$–$C_6$)alkyl, benzyloxy, substituted benzyloxy, or $NR_{11}R_{12}$, wherein $R_{11}$ and $R_{12}$ independently are hydrogen, $C_1$–$C_6$ alkyl, $C_1$–$C_6$ haloalkyl, $C_6$–$C_{10}$ aryl, $C_4$–$C_7$ cycloalkyl, $C_6$–$C_{10}$ aryl($C_1$–$C_6$)alkyl, or $R_{11}$ and $R_{12}$ are combined to form a heterocyclic ring system including pyrrolidine, piperidine, piperazine, or morpholine.

Preferred $R_1$ is H, Me, Et, t-Bu or AM. Preferred $R_2$ is fluoromethyl, acyloxymethyl, arylacyloxymethyl and aminomethyl. Preferred $R_{10}$ is benzyloxy and substituted benzyloxy. Preferred X is a peptide of 1–2 amino acids or a bond.

Exemplary preferred inhibitors of caspases having Formulae I–IV include, without limitation:

2-(Z-amino)benzoyl-Asp-fmk,
2-(Z-amino)-3-methylbenzoyl-Asp-fmk,
2-(Z-amino)-3,5-dimethylbenzoyl-Asp-fmk,
2-(Z-amino)-4-chlorobenzoyl-Asp-fmk,
2-(Z-amino)-5-chlorobenzoyl-Asp-fmk,
2-(Z-amino)-5-fluorobenzoyl-Asp-fmk,
2-(Z-amino)-6-fluorobenzoyl-Asp-fmk,
cis-2-(Z-amino)-cyclohexanecarboxyl-Asp-fmk,
2-(Z-amino)-5-methylbenzoyl-Asp-fmk,
2-(Z-amino)-6-methylbenzoyl-Asp-fmk,
2-(Z-amino)-6-chlorobenzoyl-Asp-fmk,
2-(Z-amino)-3-methoxybenzoyl-Asp-fmk,
3-(Z-amino)thiophene-2-carboxyl-Asp-fmk,
3-(methoxycarbonylamino)thiophene-2-carboxyl-Asp-fmk,
cis-2-(Z-amino)cyclopentanecarboxyl-Asp-fmk,
trans-2-(Z-amino)cyclopentanecarboxyl-Asp-fmk,
2-(Z-amino)benzoyl-Asp-DCB-methylketone,
methoxycarbonyl-Val-(2-aminobenzoyl)-Asp-fmk,
Z-Glu-(2-aminobenzoyl)-Asp-fmk, and
Z-Val-(2-aminobenzoyl)-Asp-fmk.

where Z is benzyloxycarbonyl, fmk is fluoromethylketone and DCB is 2,6-dichlorobenzoyloxy.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful arylalkyl groups include any of the above-mentioned $C_{1-10}$, alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above. Also included are the sulfoxides and sulfones of such alkylthio groups.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g. 2,6-dichlorobenzoyloxy, 2,6-difluorobenzoyloxy and 2,6-di-(trifluoromethyl)-benzoyloxy groups.

Useful amino groups include —NH$_2$, —NHR$_{11}$, and —NR$_{11}$R$_{12}$, wherein R$_{11}$ and R$_{12}$ are C$_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Optional substituents include one or more alkyl; halo; haloalkyl; cycloalkyl; aryl optionally substituted with one or more lower alkyl, halo, haloalkyl or heteroaryl groups; aryloxy optionally substituted with one or more lower alkyl, halo, haloalkyl or heteroaryl groups; aralkyl; heteroaryl optionally substitued with one or more lower alkyl, haloalkyl and aryl groups; heteroaryloxy optionally substitued with one or more lower alkyl, haloalkyl and aryl groups; alkoxy; alkylthio; arylthio; amino; acyloxy; arylacyloxy optionally substitued with one or more lower alkyl, halo alkyl and aryl groups; Diphenylphosphinyloxy optionally substituted with one or more lower alkyl, halo or haloalkyl groups; heterocyclo optionally substitued with one or more lower alkyl, halo alkyl and aryl groups; heterocycloalkyloxy optionally substitued with one or more lower alkyl, halo alkyl and aryl groups; partially unsaturated heterocycloalkyl optionally substitued with one or more lower alkyl, halo alkyl and aryl groups; or partially unsaturated heterocycloalkyloxy optionally substitued with one or more lower alkyl, halo alkyl and aryl groups. Particular examples of such optional substituents that may be present at R$_2$ include, without limitation, 3-pyrazolyloxy optionally substituted at the 2, 4 and 5-positions with lower alkyl; 3-(1-phenyl-3-trifluoromethyl)pyrazolyloxy; 2,6-di (trifluoromethyl)benzoyloxy; 2,6-dimethylbenzoyloxy, pentafluorophenoxy; 2,6-dichlorobenzoyloxy; 2-(3-(2-imidazolyl)naphthyl)oxy; diphenylphosphinyloxy; tetronyloxy; and tetramoyloxy.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy and Tris(hydroxymethyl) aminomethane (TRIS, tromethane).

Examples of prodrugs include compounds of Formulae I–IV wherein R$_1$ is an alkyl group or substituted alkyl group such as CH$_2$OCH$_3$ and CH$_2$OCOCH$_3$ (AM ester).

The invention is also directed to a method for treating disorders responsive to the inhibition of caspases in animals suffering thereof. Particular preferred embodiments of compounds for use in the method of this invention are represented by previously defined Formulae I–IV.

The compounds of this invention may be prepared using methods known to those skilled in the art. Specifically, compounds with Formulae I–IV can be prepared as illustrated by exemplary reactions in Scheme 1. The intermediate 1 was prepared according to Revesz et al. (*Tetrahedron Lett.* 35, 9693–9696, 1994). Coupling of 1 with a N-protected 2-aminobenzoic acid, which is either commercially available or which can be prepared from a commercially available 2-aminobenzoic acid, such as 2-Z-aminobenzoic acid, gave amide 2. Oxidation of 2 by Dess-Martin reagent according to Revesz et al. (*Tetrahedron Lett.* 35, 9693–9696, 1994) gave 3. Acid catalyzed cleavage of the ester gave the free acid 4.

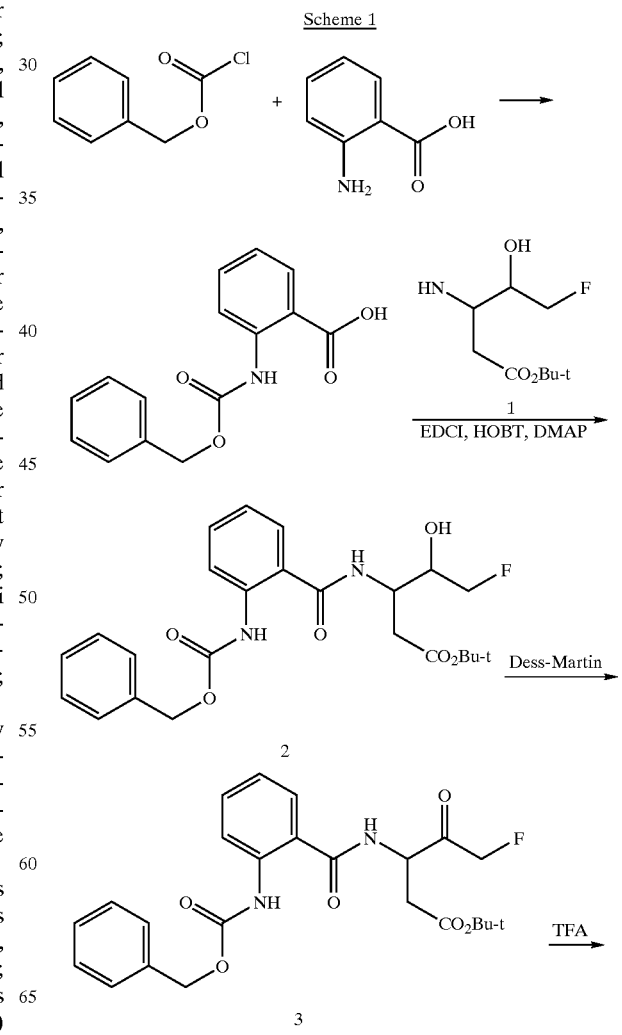

Scheme 1

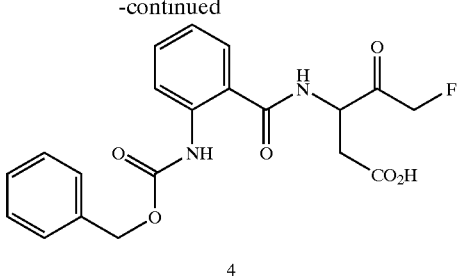

4

An important aspect of the present invention is the discovery that compounds having Formnulae I–IV are inhibitors of caspases. Therefore, these inhibitors are expected to slow or block cell death in a variety of clinical conditions in which the loss of cells, tissues or entire organs occurs.

The cell death inhibitors of the present invention can be used to reduce or prevent cell death in the nervous system (brain, spinal cord, and peripheral nervous system) under various conditions of ischemia and excitotoxicity, including, but not limited to, focal ischemia due to stroke and global ischemia due to cardiac arrest, as well as spinal cord injury (Emery et al. *J. Neurosurgery*, 89:911–920 (1998)). One particular usage is to treat the effects of oxygen deprivation which can occur during the birth of infants in high-risk labors or drowning. The cell death inhibitors can also be used to reduce or prevent cell death in the nervous system due to traumatic injury (such as head trauma), viral infection or radiation-induced nerve cell death (for example, as a side-effect of cancer radiotherapy). The cell death inhibitors can also be used to reduce or prevent cell death in a range of neurodegenerative disorders, including but not limited to Alzheimer's disease (Mattson et al. *Brain Res*. 807:167–176 (1998)), Huntington's Disease, Parkinson's Disease, multiple sclerosis, amyotrophic lateral sclerosis, and spinobulbar atrophy. The in vivo neuroprotective properties of cell death inhibitors of the invention can be tested in a rat transient focal brain ischemia model (Xue et al., *Stroke* 21:166 (1990)). The cell death inhibitors may also be used to treat or ameliorate cell death in acute bacterial meningitis.

The cell death inhibitors of the invention can be used to reduce or prevent cell death in any condition which potentially results in the death of cardiac muscle (Black et al., *J. Mol. Cel. Card*. 30:733–742 (1998) and Maulik et al. *Free Radic. Biol. Med*. 24:869–875 (1998)). This includes myocardial infarction due to myocardial ischemia and reperfusion, congestive heart failure and cardiomyopathy. One particular application is to reduce or prevent myocardial cell death as occurs in certain viral infections of the heart.

The in vivo activity of the cell death inhibitors of the invention can be tested using the "mouse liver apoptosis" model described by Rodriguez et al. (Rodriguez et al., *J. Exp. Med*., 184:2067–2072 (1996)). In this model, mice are treated intravenously,(IV) with an antiFas antibody which induces massive apoptosis in the liver and other organs, leading to generalized organ failure and death. This model is useful for indirectly testing the systemic bioavailability of the cell death inhibitors of the invention, as well as their in vivo anti-apoptotic properties. The cell death inhibitors of the invention therefore can be used to reduce or prevent apoptosis of liver cells (Jones et al. *Hepatology* 27:1632–42 (1998)) such as in sepsis (Jaeschke et al. *J. Immunol*. 160:3480–3486 (1998)) and hereditary tyrosinemia type 1 (HT1) (Kubo et al. *Prov. Natl. Acad. Sci. USA*, 95:9552–9557 (1998). The cell death inhibitors of the invention also can be used to treat hepatitis (Suzuki, *Proc. Soc. Exp. Biol. Med*. 217:450–454 (1998)); treat or ameliorate apoptotic cell death in acute pancreatitus; and treat or ameliorate organ apoptosis after burn injury.

The cell death inhibitors of the invention can be used to reduce or prevent cell death of retinal neurons (Kermer et al. *J. Neurosci*. 18:4656–4662 (1998) and Miller et al. *Am. J. Vet. Res*. 59: 149–152 (1998)) as can occur in disorders which increase intraocular pressure (such as glaucoma) or retinal disorders associated with the aging process (such as age-related macular degeneration). The inhibitors can also be used to treat hereditary degenerative disorders of the retina, such as retinitis pigmentosa.

The cell death inhibitors of the invention can also be used to reduce or prevent cell death in the kidney. This includes renal amyloidosis (Hiraoka et al. *Nippon Jinzo Gakkai Shi*, 40:276–83 (1998)), acute renal failure (Lieberthal et al. *Semin Nephrol*. 18:505–518 (1998)), murine tubular epithelial cell death induced by cyclosporine A (Ortiz et al. *Kidney International Supp*. 68: S25–S29 (1998)) and HIV-induced nephropathy (Conaldi et al. *J. Clin. Invest*. 102:2041–2049 (1998)).

The cell death inhibitors of the invention can also be used to reduce or prevent cell death of buccal mucosa due to chronic alcohol ingestion (Slomiany et al. *Biochem. Mol. Biol. Int*. 45:1199–1209 (1998)).

The cell death inhibitors of the invention can also be used to reduce or prevent cell death in plants (Richberg et al. *Curr. Opin. Plant Biol*. 1:480–485 (1998)), such as plant cell death due to pathogens (Pozo et al. *Curr. Biol*. 8:1129–1132 (1998) and Greenberg et al. *Cell*, 77:551–563 (1994)).

The cell death inhibitors of the invention can also be used to reduce or prevent cell death due to radiation and ultraviolet-irradiation (Sheikh et al. *Oncogene*, 17:2555–2563 (1998)).

The cell death inhibitors of the invention can also be used to reduce or prevent apoptotic death of bone marrow cells in myelodysplastic syndromes (MDS) (Mundle et al., *Am. J. Hematol*. 60:36–47 (1999)).

The cell death inhibitors of the invention can also be used to reduce or prevent premature death of cells of the immune system, and are particularly useful in treating immune deficiency disorders, such as acquired immune deficiency syndrome (AIDS), severe combined immune deficiency syndrome (SCIDS) and related diseases. The cell death inhibitors can also be used to treat radiation-induced immune suppression.

Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium. Cell death inhibitors may also be used to reduce or prevent cell death in the donor organ/tissue after it has been transplanted to protect it from the effects of reperfusion injury and/or effects of host immune cells which kill their targets by triggering apoptosis. The cytoprotective effects of cell death inhibitors can also be used to prevent the death of human or animal sperm and eggs used in in vitro fertilization procedures. These inhibitors can be used during the harvesting process and can also be included in the storage medium.

Mammalian cell lines, insect cells and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including these cell death inhibitors in the growth medium in a concentration range of 1–100 μM.

The factors governing hair growth and loss are largely unknown. There is some evidence, however, that hair follicle regression (referred to as catagen) may be due at least partially to apoptosis. Therefore, it is contemplated that the cell death inhibitors of the present invention can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is contemplated that the cell death inhibitors of the present invention can also be used in treating or preventing cases of premature graying of the hair.

The death of skin epithelial cells can occur after exposure to high levels of radiation, heat or chemicals. It is contemplated that the cell death inhibitors of the present invention can be used to treat, reduce or prevent this type of skin damage. In one particular application, the cell death inhibitors can be applied as part of a topical formulation, e.g. an ointment, to treat acute over-exposure to the sun and to prevent blistering and peeling of the skin.

Goldberg et al. (*Nature Genetics* 13:442–449 (1996)) reported recently that huntingtin, a protein product of Huntington's disease (HD) gene, can be cleaved by CPP32 but not ICE. The mutation underlying HD is an expansion of a CAG trinucleotide at the 5' end of the HD gene. The trinucleotide expansion exceeding 36 repeats is associated with the clinical presentation of HD. The CAG expansion promotes cleavage of huntingtin by CPP32, thus links the role of CPP32 in the apoptotic cell death in HD. Compounds of the present invention with CPP32 inhibiting activity will be useful in blocking CPP32 induced apoptotic cell death, thus in preventing and treating HD and other disorders characterized by expansion of trinucleotide repeats such as myotonic dystrophy, fragile X mental retardation, spinobulbar muscular atrophy, spinocerebellar atoxia type I and Dentato-Rubro pallidoluysian atrophy.

The invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a caspase inhibitor.

When animals are treated with chemotherapeutic agents and/or radiation to kill cancer cells, an unwanted side effect is the apoptotic death of rapidly dividing non-cancer cells. Such non-cancer cells include cells of the gastrointestinal tract, skin, hair, and bone marrow cells. According to the present invention, caspase inhibitors are administered to such non-cancer cells to prevent apoptosis of such cells. In a preferred embodiment, the caspase inhibitors are administered locally, e.g. to the gastrointestinal tract, mouth, skin or scalp to prevent apoptosis of the gastrointestinal, mouth, skin or hair cells but allowing for the death of the cancer cells. Thus, in one example, it is possible to treat brain cancer with chemotherapy or radiation therapy and protect the outer skin, hair cells, gastrointestinal tract and bone marrow by local administration of a caspase inhibitor. In the case of oral mucositis, the caspase inhibitor can be applied, for example, in the form of a mouth wash or mouth rinse, in a gel, or in the form of an oral slow release lozenge to prevent activation of caspases and apoptotic cell death induced by the chemotherapeutic agent or by radiation. In the case of gastrointestinal mucositis, the caspase inhibitor can be applied in a form such that it is not absorbed systemically or in a form that coats the surface of the gastrointestinal tract, or a suppository formulation for the treatment of gastrointestinal mucositis. In the case of proctitis, the capsase inhibitor may be applied as part of an enema or suppository. In the case of bladder mucositis, the caspase inhibitor may be applied though a bladder catheter. For prevention of radiation or chemotherapy-induced hair loss, the caspase inhibitor can be applied, for example, to the scalp in the form of a hair rinse, hair gel, shampoo or hair conditioner. Importantly, the caspase inhibitor can be applied prior to the administration of the chemotherapeutic agent or radiation, thus preventing the onset of the damaging effects of the chemotherapeutic agent or radiation to the normal cells.

The cell death inhibitors of the present invention may also be used to treat or prevent the inflammatory response in psoriasis or inflammatory bowel disease.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for apoptosis-mediated disorders, e.g., neuronal cell death, heart disease, retinal disorders, polycystic kidney disease, immune system disorders and sepsis. Preferably, about 0.01 to about 10 mg/kg is orally administered to treat or prevent such disorders. For intramuscular injection, the dose is generally about one-half of the oral dose. For example, for treatment or prevention of neuronal cell death, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07–1.0 mg/ml, more preferably, about 0.1–0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular cell death inhibitors of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular cell death inhibitors of the present invention with a solution of a pharmaceutically acceptable non-toxic base such as sodium hydroxide, potassium hydroxide, choline hydroxide, sodium carbonate Tris and the like.

The pharmaceutical compositions of the invention may be administered to any animal which may experience the beneficial effects of the compounds of the invention. Foremost among such animals are mammals, e.g., humans, although the invention is not intended to be so limited.

The caspase inhibitors and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired. In general, the caspase inhibitors are administered locally to the tissues that are to be protected from apoptosis and separately from the chemotherapeutic agent. For example, cisplatin may be administered by i.v. injection to treat a cancer such as brain, lung, breast, liver, kidney, pancreatic, ovarian, prostatic cancer, and the caspase inhibitor administered locally to treat, ameliorate, or prevent apototic cell death in the mouth or gastrointestinal tract, such as a mouth wash for the treatment of oral mucositis; and IV injectable aqueous solution for the treatment of bone marrow cell death; and an oral formulation suitable for coating the gastrointestinal surfaces or an emema or suppository formulation for the treatment of gastrointestinal mucositis including proctitis. The caspase inhibitors may also be applied through a bladder catheter for the treatment, amelioration or prevention of bladder mucositis. Alternatively or concurrently, the caspase inhibitors may be applied topically to the skin and/or scalp to treat, ameliorate or prevent apoptotic cell death of hair and skin cells. In a further embodiment, the chemotherapeutic agent or radiation may be applied locally to treat a localized cancer such as brain, lung, breast, liver, kidney, pancreatic, ovarian, prostatic cancer, and the caspase inhibitor administered systemically, e.g. by i.v. injection, to treat, ameliorate or prevent apoptotic cell death of the gastrointestinal tract cells, mouth epithelial cells, bone marrow cells, skin cells and hair cells. In the case of oral mucositis in brain cancer treatment, for example, a caspase inhibitor that does not penetrate the blood-brain barrier can be applied, for example, systemically by i.v. injection followed by irradiation of the brain tumor. This would protect the oral mucosa from the harmful effects of radiation but the caspase inhibitor would not protect the brain tumor from the therapeutic effects of radiation. Importantly, the caspase inhibitor can be applied prior to administration of the radiation, thus preventing the onset of the damaging effects of the radiation to the normal mucosa cells.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin damage, such as that caused by exposure to high levels of radiation, including ultraviolet radiation, heat or chemicals.

One or more additional substances which have therapeutic effects on the skin may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, growth factors, wound sealants, carriers, etc., that are known or apparent to those skilled in the art. The compositions of the invention are administered to a warm-blooded animal, such as human, already suffering from a skin damage, such as a burn, in an amount sufficient to allow the healing process to proceed more quickly than if the host were not treated. Amounts effective for this use will depend on the severity of the skin damage and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

When the compounds are to be administered to plants, they may be applied to the leaves and/or stems and/or flowers of the plant, e.g. by spraying. The compounds may be spayed in particulate form or dissolved or suspended in an appropriate carrier, e.g. in water or an oil-water emulsion. The compounds may also be combined with the soil of the plant. In this embodiment, the compounds are taken up by the roots of the plant.

In a preferred embodiment, the caspase inhibitor is formulated as part of a mouthwash for the treatment, amelioration or prevention of oral mucositis. Such mouthwashes are aqueous solutions of the caspase inhibitor which may also contain alcohol, glycerin, synthetic sweeteners and surface-active, flavoring and coloring agents. They may also contain anti-infective agents such as hexetidine and cetylpyridinium chloride. The mouthwashes may also contain topical anesthetics (e.g. benzocaine, cocaine, dyclonine hydrochloride, lidocaine, proparacaine hydrochloride or teracaine hydrochloride), for example, for relieving pain of radiation or chemotherapy-induced sores. The mouth washes may have either acidic or basic pH. See Remington's Pharmaceutical Sciences, A. R. Gennaro (ed.), Mack Publishing Company, pp. 1045, 1046, 1526 and 1965 (1990).

In another preferred embodiment, the caspase inhibitor is formulated as an oral formulation which is capable of coating the gastrointestinal surfaces for the treatment, amelioration or prevention of gastrointestinal mucositis. Examples of gastrointestinal mucositis include esophageal mucositis, gastric mucositis, and intestinal mucositis. Such formulations may comprise gastric antacids such as aluminum carbonate, aluminum hydroxide gel, bismuth subnitrate, bismuth subsalicylate, calcium carbonate, dihydroxyaluminum sodium carbonate, magaldrate, magnesium carbonate, magnesium hydroxide, magnesium oxide, sodium bicarbonate, milk of bismuth, dihydroxyaluminum aminoacetate, magnesium phosphate, magnesium trisilicate and mixtures thereof. Other additives include without limitation $H_2$-receptor antagonists, digestants, anti-emetics, adsorbants, and miscellaneous agents. See Remington's Pharmaceutical Sciences, A. R. Gennaro (ed.), Mack Publishing Company, pp. 774–778 (1990).

Chemotherapy agents such as cisplatin and radiation therapy often induce early and late onset emesis in the patient. Thus, in one embodiment an antiemetic is coadministered together with the caspase inhibitor to avoid emesis and retain contact of the caspase inhibitor with the gastrointestinal tract. Examples of such antiemetics include without limitation compounds that block the dopaminergic emetic receptors such as metoclopramide and trimethobenzamide, and cannabinoids. Metoclopramide may be administered orally prior to and/or during chemotherapy/radiation therapy/caspase inhibitor therapy to prevent the early emesis response and then later by intranasal administration according to U.S. Pat. Nos. 5,760,086 and 4,536,386 to prevent delayed onset emesis. During the period after chemotherapy/radiation therapy, both the caspase inhibitor and the antiemetic may be coadministered to treat, ameliorate or prevent gastrointestinal mucositis.

In a further embodiment, the caspase inhibitor may be formulated as an IV injectable solution for the treatment, amelioration or prevention of bone marrow cell death.

The compositions may be administered to a warm-blooded animal, such as human, already suffering from chemotherapy or radiation therapy-induced non-cancer cell death, or, more preferably, before or during therapy with chemotherapy or radiation.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

2-(Z-Amino)benzoyl-Asp-fmk

Step A. 2-Z-Aminobenzoic acid. To a solution of 2-aminobenzoic acid (0.30 g, 2.2 mmol) in pyridine (2 mL) was added benzyl chloroformate (0.6 mL, 4.2 mmol) at 0° C. The mixture was then stirred at room temperature for 1 h, diluted with EtOAc (50 mL), washed with 2N HCl, water and brine, dried over $Na_2SO_4$ and concentrated in vacuo. The crude solid was washed with 4:1 hexane/EtOAc twice and dried in vacuo to yield the title compound as a white solid (270 mg, 1.0 mmol, 45%). $^1$H NMR (DMSO-$d_3$): δ 11.49 (br s, 1H), 8.22 (d, J=7.5, 1H), 7.95 (d, J=7.5, 1H), 7.51 (t, J=7.5, 1H), 7.39–7.32 (m, 5H), 7.05 (d, J=7.5, 1H), 5.15 (s, 2H).

Step B. tert-Butyl 5-fluoro-3-[2-Z-aminobenzoylamido]-4-hydroxypentanoate. A mixture of 2-Z-aminobenzoic acid (90 mg, 0.33 mmol), 1-(3-dimethylaminopropyl)-3-ethylcarbodiimide hydrochloride (EDCI, 61 mg, 0.40 mmol), 1-hydroxybenzotriazole hydrate (HOBT, 73 mg, 0.38 mmol), dimethylaminopyridine (DMAP, 22 mg, 0.18 mmol) and tert-butyl 3-amino-5-fluoro-4-hydroxypentanoate (79 mg, 0.38 mmol) in THF (10 mL) was stirred at room temperature for 20 h, diluted with 1:1 hexane/EtOAc (75 mL), washed with water, 2N HCl, water, 2N NaOH and brine, dried over $Na_2SO_4$ and cocentrated in vacuo. The residue was purified by chromatography (3:2 Hexane/EtOAc) to yield the title compound as a yellow hydroscopic solid (52 mg, 0.11 mmol, 33%).

Step C. 2-(Z-Amino)benzoyl-Asp(OBu-t)-fmk. A mixture of periodinane (0.41 g, 0.97 mmol) and tert-butyl 5-fluoro-3-[2-Z-aminobenzoylamido]-4-hydroxypentanoate (52 mg, 0.11 mmol) in dichloromethane (15 mL) was refluxed for 20 h, cooled to room temperature, and 25 mL of saturated sodium bicarbonate aqueous solution containing 1.0 g of $Na_2S_2O_3$ was added. The resulting mixture was stirred for 2 h, diluted with 1:1 hexane/EtOAc (75 mL), washed with water and brine, dried over $Na_2SO_4$ and concentrated in vacuo. The residue was purified by chromatography (3:2 hexane/EtOAc) to yield the title compound as a hydroscopic yellow solid (45 mg, 0.10 mmol, 91%). $^1$H NMR (CDCl$_3$): δ 10.48 (s, 1H), 8.42 (d, J=8.7, 1H), 7.51–7.33 (m, 7H), 7.07 (m, 1H), 5.30–4.98 (m, 1H), 5.21 (s, 2H), 3.11–2.83 (m, 2H), 1.44 (s, 9H).

Step D. 2-(Z-Amino)benzoyl-Asp-fmk To a solution of 2-(Z-Amino)benzoyl-Asp(OBu-t)-fmk (45 mg, 0.10 mmol) in 5 mL of $CH_2Cl_2$ was added 1 mL of TFA. The resulting solution was allowed to stir at rt for 1 hr, diluted with EtOAc (75 ml), washed with water, aqueous $Na_2HPO_4$ to pH 5 and then brine, dried over $Na_2SO_4$ and concentrated in vacuo to give the title compound as a white solid, (15 mg, 0.037 mmol, 38%). $^1$H NMR (DMSO-$d_6$): δ 10.63 (s, 1H), 9.08 (s, 1H), 8.14 (d, J=7.8, 1H), 7.76 (d, J=7.8, 1H), 7.54 (t, J=7.8, 1H), 7.41–7.35 (m, 5H), 7.15 (t, J=7.8, 1H), 5.16 (s, 2H), 5.26–4.95 (m, 2H), 4.83 (m, 1H), 3.00–2.64 (m, 2H).

EXAMPLE 2

2-(Z-Amino)-6-methylbenzoyl-Asp-fmk

The title compound was prepared in four-steps as described in Example 1 from 2-amino-6-methylbenzoic acid. $^1$H NMR (DMSO-$d_6$): δ 8.85 (s, 1H), 8.68 (s, 1H), 7.49–7.01 (m, 8H), 5.12 (s, 2H), 4.82 (m, 1H), 5.26–4.95 (m, 2H), 3.00–2.64 (m. 2H), 2.26 (s, 3H).

EXAMPLE 3

2-(Z-Amino)-5-methylbenzoyl-Asp-fmk

The title compound was prepared in four-steps as described in Example 1 from 2-amino-5-methylbenzoic acid. $^1$H NMR (DMSO-$d_6$): δ 10.48 (s, 1H), 9.10 (d, J=9, 1H), 8.00 (d, J=8.7, 1H), 7.89 (s, 1H), 7.58 (s, 1H), 7.41–7.34 (m, 5H), 5.14 (s, 2H), 4.83 (m, 1H), 5.39–4.41 (m, 2H), 2.94–2.80 (m. 2H), 2.30 (s, 3H).

EXAMPLE 4

2-(Z-Amino)-3-methylbenzoyl-Asp-fmk

The title compound was prepared in four-steps as described in Example 1 from 2-amino-3-methylbenzoic acid. $^1$H NMR (DMSO-$d_6$): δ 9.05 (s, 1H), 8.73 (s, 1H), 7.38–7.20 (m, 8H), 5.08 (s, 2H), 4.72 (m, 1H), 5.32 (bs, 2H), 2.81–2.66 (m. 2H), 2.21 (s, 3H).

EXAMPLE 5

2-(Z-Amino)-3-methoxybenzoyl-Asp-fmk

The title compound was prepared in four-steps as described in Example 1 from 2-amino-3-methoxybenzoic acid. $^1$H NMR (DMSO-$d_6$): δ 8.73 (bs, 1H), 8.64 (bs, 1H), 7.57–7.06 (m, 9H), 5.06 (s, 2H), 4.72 (bs, 1H), 5.26–4.97 (m, 2H), 3.78 (s, 3H), 2.78–2.66 (m. 2H).

EXAMPLE 6

2-(Z-Amino)-5-fluorobenzoyl-Asp-fmk

The title compound was prepared in four-steps as described in Example 1 from 2-amino-5-fluorobenzoic acid. $^1$H NMR (DMSO-$d_6$): δ 10.40 (bs, 1H), 9.13 (bs, 1H), 8.07 (q, J=5.1, 1H), 7.61 (d, J=6.6, 1H), 7.46–7.33 (m, 6H), 5.15 (s, 2H), 4.81 (bs, 1H), 2.84–2.72 (m. 2H).

EXAMPLE 7 cis-2-(Z-Amino)cyclohexanecarboxyl-Asp-fmk

The title compound was prepared in four-steps as described in Example 1 from cis-2- aminocyclohexanecarboxylic acid. $^1$H NMR (DMSO-d$_6$): δ 8.28 (bs, 1H), 7.39–7.09 (m, 5H), 4.98 (s, 2H), 4.52–4.45 (m, 1H), 3.99 (bs, 1H), 2.62–2.53 (m, 4H), 1.77–1.23 (m, 8H).

EXAMPLE 8

2-(Z-Amino)-3,5-dimethylbenzoyl-Asp-fmk

The title compound was prepared in four-steps as described in Example 1 from 2-amino-3,5-dimethylbenzoic acid. $^1$H NMR (DMSO-d$_6$): δ 8.05 (s, 1H), 7.42–7.17 (m, 8H), 5.15 (s, 2H), 5.19–5.03 (m, 2H), 4.87 (m, 1H), 2.30 (s, 3H), 2.26 (s, 3H).

EXAMPLE 9

2-(Z-Amino)-5chlorobenzoyl-Asp-fmk

The title compound was prepared in four-steps as described in Example 1 from 2-amino-5-chlorobenzoic acid. $^1$H NMR (DMSO-d$_6$): δ 10.56 (s, 1H), 9.19 (s, 1H), 8.15 (d, J=9.0, 1H), 7.84 (s, 1H), 7.61 (d, J=9.0, 1H), 7.41–737 (m, 5H), 5.16 (s, 2H), 4.81 (m, 1H), 5.41–4.80 (m, 2H), 2.84–2.73 (m, 2H).

EXAMPLE 10

2-(Z-Amino)-6-chlorobenzoyl-Asp-fmk

The title compound was prepared in four-steps as described in Example 1 from 2-amino-6-chlorobenzoic acid. $^1$H NMR (DMSO-d$_6$): δ 9.17 (d, J=4.2, 1H), 8.95 (s, 1H), 7.74–7.24 (m, 8H), 5.50–5.21 (m, 2H), 5.15 (s, 2H), 4.85–4.78 (m, 1H), 2.98–2.65 (m, 2H).

EXAMPLE 11

2-(Z-Amino)-4-chlorobenzoyl-Asp-fmk

The title compound was prepared in four-steps as described in Example 1 from 2-amino-3,5-dimethylbenzoic acid. $^1$H NMR (DMSO-d$_6$): δ 10.84 (s, 1H), 9.19 (s, 1H), 8.24 (s, 1H), 7.81 (d, J=8.4, 1H), 7.42–7.24 (m, 6H), 5.18 (s, 2H), 5.25–5.20 (m, 2H), 4.82 (m, 1H), 2.94–2.63 (m, 2H).

EXAMPLE 12

3-(Z-Amino)thiophene-2-carboxyl-Asp-fmk

Step A. 3-(Z-Amino)thiophene-2-carboxylic acid. The mixture of methyl 3-aminothiophene-2-carboxylate (0.2 g, 1.27 mmol) in 2N NaOH (10 mL) was heated at 90° C. for 15 min, then cooled to 0° C. To the resulting solution was added benzyl chloroformate (1.5 mL, 10.5 mmol) and THF (10 mL). The mixture was then stirred at room temperature for 1 h, washed with 3:1 hexane: ethyl acetate (2×15 mL). The aqueous phase was acidified with 2N HCl to pH~1–2, extracted with ethyl acetate (3×15 mL), washed with water and brine, dried over Na$_2$SO$_4$ and concentrated in vacuo to yield the title compound as a white solid (70 mg).

The title compound was then prepared in three steps as described in Example 1 (B–D). $^1$H NMR (DMSO-d$_6$): δ 10.43 (s, 1H), 8.74 (s, 1H), 7.81 (d, J=5.4, 1H), 7.73 (d, J=5.4, 1H), 7.44–7.35 (m, 5H), 5.18 (s, 2H), 5.32–5.04 (m, 2H), 4.79 (m, 1H), 2.88–2.67 (m, 2H).

EXAMPLE 13

3-(Methoxycarbonylamino)thiophene-2-carboxyl-Asp-fmk

The title compound was prepared in four-steps as described in Example 12 from methyl 3-aminothiophene-2-carboxylate and methyl chloroformate. $^1$H NMR (DMSO-d$_6$): δ 10.34 (s, 1H), 8.70 (s, 1H), 7.79 (d, J=5.7, 1H), 7.72 (d, J=5.7, 1H), 5.31–4.80 (m, 3H), 3.70 (s, 3H), 2.96–2.73 (m, 2H).

EXAMPLE 14

Cis-2-(Z-Amino)cyclopentanecarboxyl-Asp-fmk

The title compound was prepared in four-steps as described in Example 1 from cis-2-aminocyclopentanecarboxylic acid. $^1$H NMR (DMSO-d$_6$): δ 8.35 (s, 1H), 7.34–7.28 (m, 5H), 7.09 (m, 1H), 5.13–4.50 (m, 5H), 4.11 (m, 1H), 2.81 (m, 1H), 2.73–2.51 (m, 2H), 1.91–1.40 (m, 6H).

EXAMPLE 15

Trans-2-(Z-Amino)cyclohexanecarboxyl-Asp-fmk

The title compound was prepared in four-steps as described in Example 1 from trans-2-aminocyclohexanecarboxylic acid. $^1$H NMR (DMSO-d$_6$): δ 12.48 (s, 1H), 8.26–8.15 (m, 1H), 7.38–7.17 (m, 5H), 5.18–4.47 (m, 5H), 2.67–2.50 (m, 2H), 2.19 (m, 1H), 1.83–1.06 (m, 10H).

EXAMPLE 16

Z-Glu-(2-aminobenzoyl)-Asp-fmk

Step A. Z-Glu(OBu-t)-2-aminobenzoic acid. To a solution of Z-Glu(OBu-t)OH (272 mg, 0.81 mmol) in THF (5 mL) was added N-methylmorpholine (110 μL, 1.1 mmol) at –45° C., followed by isobutyl chloroformate (105 μL, 0.81 mmol). The mixture was stirred at –45 ° C. for 30 min. and a solution of anthranllic acid (127 mg, 0.93 mmol) in THF (5 mL) was added, followed by more N-methylmorpholine (200 μL, 1.82 mmol). The resulting mixture was stirred overnight and the cooling bath was allowed to slowly warm to room temperature. After diluted with EtOAc (100 mL), the mixture was washed with 2N HCl, water, saturated NaHCO$_3$, water, 2N HCl, water and brine, dried over Na$_2$SO$_4$ and concentrated in vacuo to yield the product as a highly hydroscopic white solid (330 mg, 0.72 mmol, 89%). $^1$H NMR (DMSO-d$_6$): δ 1.79 (s, 1H), 8.59 (d, J=8.6, 1H), 8.00 (t, J=6.0, 1H), 7.60 (t, J=8.6, 1H), 7.39–7.31 (m, 5H), 7.17 (t, J=7.8, 1H), 5.16–4.99 (m, 2H), 4.08 (m, 1H), 2.33 (m, 2H), 2.08–1.75 (m, 2H), 1.38 (s, 9H).

Step B. tert-Butyl 5-fluoro-3-[Z-Glu(OBu-t)-(2-aminobenzoyl)amido]-4-hydroxypentanoate. A mixture of Z-Glu(OBu-t)-2-aminobenzoic acid (330 mg, 0.72 mmol), EDCI (129 mg, 0.67 mmol), HOBT (104 mg, 0.68 mmol), DMAP (46 mg, 0.38 mmol) and tert-butyl 3-amino-5-fluoro-4-hydroxypentanoate (136 mg, 0.66 mmol) in THF (6 mL) was stirred at room temperature for 20 h. After diluted with 1:1 hexane/EtOAc (75 mL), the mixture was washed with water, 2N HCl, water, 2N NaOH and brine, dried over Na$_2$SO$_4$ and concentrated in vacuo. The residue was purified by chromatography (3:1 then 3:2 hexane/EtOAc) to yield the title compound as a white solid (45 mg, 0.068 mmol, 10%).

Step C. Z-Glu(OBu-t)-[2-aminobenzoyl]-Asp(OBu-t)-fmk The title compound was synthesized by a similar procedure as described in Step C, Example 1 in 58% yield.

Step D. Z-Glu-[2-aminobenzoyl]-Asp-fmk. The title compound was synthesized by a similar procedure as described in Step D, Example 1 in 14% yield. $^1$H NMR (DMSO-d$_6$): δ 1.46 (s, 1H), 9.18 (s, 1H), 8.57–7.20 (m, 6H), 5.36–4.84 (m, 5H), 4.04 (br s, 1H), 2.95–1.81 (m, 6H).

EXAMPLE 17

Z-Val-(2-Aminobenzoyl)-Asp-fmk

The title compound was synthesized as described in Example 16 from Z-Val. $^1$H NMR (DMSO-d$_6$): δ 1.34–11.25 (m, 1H), 9.17–7.17 (m, 11H), 5.42–4.30 (m, 5H), 3.95–3.75 (m, 1H), 2.95–2.57 (m, 2H), 1.92 (m, 1H), 0.91–0.84 (m, 6H).

EXAMPLE 18

2-(Z-Amino)benzoyl-Asp-DCB-methylketone

Step A. Z-Asp(OBu-t)-DCB-methylketone To a solution of Z-Asp(OBu-t)-bromomethylketone (500 mg, 1.24 mmol) in DMF (10 ml) was added potassium fluoride (320 mg, 5.50 mmol), and 2,6-dichlorobenzoic acid (348 mg, 1.82 mmol). The mixture was stirred at room temperature for 12 h, and then was diluted with 25 ml of ethyl acetate, washed with aqueous NH$_4$Cl and brine, dried over Na$_2$SO$_4$ and concentrated in vacuo. The title compound was obtained as white solid (0.78 g, 2.62 mmol, 69%). $^1$H NMR (CDCl$_3$): 7.34 (m, 8H), 5.96 (d, J=8.7, 1H), 5.21 (d, J=6.6, 2H), 5.16 (s, 2H), 4.70 (m, 1H), 2.88 (m, 2H), 1.27 (s, 9H).

Step B. Asp(OBu-t)-DCB-methylketone-HCl To a solution of Z-Asp(OBu-t)-DCB-methylketone (572 mg, 1.14 mmol) in ethanol (15 ml) was added Pd/C (50 mg) and 6N HCl (0.2 ml). The mixture was stirred at room temperature under H$_2$ atmosphere (1 atm) for 12 h, then it was filtered and concentrated. The title compound was obtained as pale white solid (416 mg, 1.04 mmol, 90%). $^1$H NMR (CDCl$_3$): 7.27 (m, 3H), 5.28 (m, 2H), 4.94 (m, 1H), 3.27 (m, 2H), 1.42 (s, 9H).

Step C. 2-(Z-Amino)benzoyl-Asp(OBu-t)-DCB-methylketone To a solution of 2-(Z-amino)benzoic acid (140 mg, 0.52 mmol) in THF (5 mL) was added N-methylmorpholine (65 μL, 0.59 mmol), followed by 2-methylpropyl chloroformate (70 μL, 0.54 mmol) at −45° C. After 30 min., a solution of Asp(OBu-t)-DCB-methylketone-HCl (121 mg, 0.27 mmol) in THF (5 mL) was added to the solution. The resulting mixture was further stirred overnight and the cooling bath was allowed to slowly warm to room temperature. It was then diluted with 1:1 hexane/EtOAc (100 mL), washed with water, 2N NaOH and brine, dried over Na$_2$SO$_4$ and concentrated in vacuo. The residue was purified by chromatography (3:1 hexane/EtOAc) to yield the title compound as a white solid (365 mg, 0.05 mmol, 19%). $^1$H NMR (CDCl$_3$): 10.90 (s, 1H), 8.49 (d, J=7.5, 1H), 7.87 (dd, J=8.1, 1.8, 1H), 7.56–7.32 (m, 9H), 7.08 (t, J=6.9, 1H), 5.23 (s, 2H), 5.28 (m, 1H), 4.90 (d, J=1.8, 2H), 3.16–2.91 (m, 1H), 1.43 (m, 9H).

Step D. 2-(Z-Amino)benzoyl-Asp-DCB-methylketone A solution of 2-(Z-amino)benzoyl-Asp(OBu-t)-DCB-methylketone (35 mg) and TFA (1 mL) in methylenechloride (3 mL) was stirred at room temperature for 2 h. The mixture was diluted with EtOAc (70 mL), washed with saturated Na$_2$HPO$_4$ to pH~5, and further washed with water, and brine, dried over Na$_2$SO$_4$ and concentrated in vacuo to yield the title compound as a white solid (10 mg, 0.016 mmol, 33%). $^1$H NMR (CDCl$_3$): 10.94 (s, 1H), 8.49 (d, J=8.4, 1H), 7.87 (dd, J=8.1, 1.5, 1H), 7.53 (m, 1H), 7.45–7.33 (m, 8H), 7.07 (m, 1H), 5.22 (s, 2H), 5.10–5.07 (m, 1H), 4.90 (m, 2H), 3.11 (dd, J=8.4, 19.0, 1H), 2.95 (dd, J=1.8, 19.0, 1H)).

EXAMPLE 19

Methoxycarbonyl- Val-(2-aminobenzoyl)-Asp-fmk

Step A. tert-Butyl 5-fluoro-3-(2-aminobenzoylamido)-4-hydroxypentanoate.HCl. A mixture of tert-butyl 5-fluoro-3-(2-Z-aminobenzoylamido)-4-hydroxypentanoate (80 mg, 0.174 mmol), Pd-C (23mg) and 6N HCl (0.087 mL) in ethanol (5 mL) was stirred under hydrogen atmosphere at room temperature for 2 h. The mixture was filtered and the solvent was evaporated to yield the title product. It was used in next step without further purification.

Step B. tert-Butyl 5-fluoro-3-(methoxycarbonyl-Val-2-aminobenzoylamido)-4-hydroxypentanoate. To a solution of methoxycarbonyl-Val-OH (31 mg, 0.1 7 mmol) in THF (5 mL) was added N-methylmorpholine (38 μL, 0.34 mmol) at −45° C., followed by isobutyl chloroformate (45 μL, 0.034 mmol). The mixture was stirred at −45° C. for 30 min and a solution of tert-butyl 5-fluoro-3-(2-aminobenzoylamido)-4-hydroxypentanoate.HCl in THF (5 mL) was added, followed by more N-methylmorpholine (50 μL, 0.45 mmol). The resulting mixture was stirred overnight and the cooling bath was allowed to slowly warm to room temperature. After dilution with ethyl acetate (50 mL), the mixture was washed with water and brine, dried over Na$_2$SO$_4$ and concentrated in vacuo. The residue was purified by chromatography (3:2 hexane: ethyl acetate) to yield the title compound as a white hydroscopic solid (20 mg, 0.041 mmol, 24%). $^1$H NMR (CDCl$_3$): δ 1.36–11.24 (m, 1H), 8.54 (d, J=8.7, 1H), 7.55–7.05 (m, 4H), 5.40 (m, 1H), 4.89–3.85 (m, 6H), 3.71 (d, J=1.8, 3H), 2.84–2.61 (m, 2H), 2.29 (m, 1H), 1.46–1.44 (m, 9H), 1.05–0.98 (m, 6H).

Step C, D. Methoxycarbonyl-Val-(2-aminobenzoyl)-Asp-fmk The title compound was synthesized with a similar procedure as described in Step C and D of example 1. $^1$H NMR (DMSO-d$_6$): δ 2.52 (s, 1H), 11.27 (d, J=6.0, 1H), 9.18 (m, 1H), 7.88–7.54 (m, 4H), 7.20 (t, J=7.5, 1H), 5.39–4.44 (m, 3H), 3.83 (m, 1H), 3.57 (d, J=2.4, 3H), 2.96–2.65 (m, 2H), 2.18 (m, 1H), 0.92 (t, J=6.3, 6H).

EXAMPLE 20

Enzyme Activity

The activity of 2-(Z-amino)benzoyl-Asp-fmk as an inhibitor of caspase-3 was measured in a fluorometric enzyme assay. Enzyme activity was measured using synthetic peptide substrates attached to a fluorogenic leaving group. Cleavage of the synthetic substrate by the enzyme results in a fluorescent signal which is read in a spectrofluorometer or in a fluorometric microtiter plate reader.

Twelve concentrations of the testing compound ranged from 30 pM to 10 μM were tested in the enzyme assay. The enzyme reaction was conducted in the presence of 2 ng rCaspase 3 (purchased from PharMingen, a Becton division company, San Diego, Calif.), various concentrations of testing compound, 10 μM caspase 3 substrate Ac-DEVD-AMC (SEQ ID NO:1) (purchased from Quality Controlled Biochemicals, Inc., Hopkinton, Mass.) and caspase buffer (20 mM PIPES, 100 mM NaCl, 10 mM DTT, 1 mM EDTA, 0.1% CHAPS and 10% sucrose, pH 7.2) in a total volume of 100 μL. The enzyme reaction was carried out in a 96-well plate and incubated at 37° C. for 30 minutes. The plate was then read with a fluorescence plate reader (EG&G WALLAC 1420-002) using excitation filter at 355 nm/emission filter at 460 nm. The data was analyzed using GraphPrism software to give an IC$_{50}$ value of 0.2 μM.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications

What is claimed is:

1. A compound having the Formulae I or II or III:

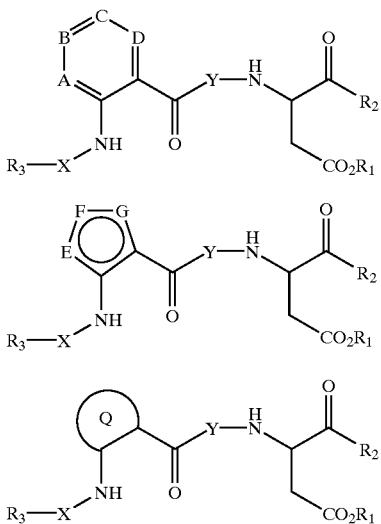

or a pharmaceutically acceptable salt or prodrug thereof, wherein:

$R_1$ is an optionally substituted alkyl or hydrogen;

$R_3$ is an N-protecting group;

$R_2$ is hydrogen or optionally substituted alkyl;

Q is an optionally substituted saturated or partially saturated carbocycle or heterocycle;

X is a peptide of 1–4 amino acids or a bond;

Y is a peptide of 1–4 amino acids or a bond;

A is $CR_6$ or nitrogen;

B is $CR_7$ or nitrogen;

C is $CR_8$ or nitrogen;

D is $CR_9$ or nitrogen;

provided that not more than two of A, B, C or D is nitrogen; and $R_6$–$R_9$ independently are hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle;

E is $C_{14}$, nitrogen, oxygen or sulfur;

F is $C_{15}$, nitrogen, oxygen or sulfur;

G is $C_{16}$, nitrogen, oxygen or sulfur;

provided that only one of E, F, G is nitrogen, oxygen or sulfur and $R_{14}$–$R_{16}$ are independently hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_{14}$ and $R_{15}$, or $R_{15}$ and $R_{16}$, are taken together with the carbon atoms to which they are attached to form a carbocycle or heterocycle.

2. A compound according to claim 1, wherein $R_3$ is t-butyloxycarbonyl, acetyl or benzyloxycarbonyl.

3. A compound according to claim 1, wherein $R_1$ is H, Me, Et or acetoxymethyl.

4. A compound according to claim 1, wherein $R_2$ is hydrogen, fluoromethyl, acyloxymethyl, arylacyloxymethyl or aminomethyl.

5. A compound according to claim 1, wherein X is a bond.

6. A compound according to claim 1, wherein A, B, C and D are CH.

7. A compound according to claim 1, wherein A is nitrogen, and B, C and D are CH.

8. A compound according to claim 1, wherein G is sulfur, and E and F are CH.

9. A compound according to claim 1, wherein Q is cyclohexyl or cyclopentyl.

10. A compound according to claim 1, wherein said compound is selected from the group consisting of:

2-(Z-amino)benzoyl-Asp-fmk, 2-(Z-amino)-3-methylbenzoyl-Asp-fmk,
2-(Z-amino)-3,S-dimethylbenzoyl-Asp-fmk,
2-(Z-amino)-4-chlorobenzoyl-Asp-fmk,
2-(Z-amino)-5-chlorobenzoyl-Asp-fmk,
2-(Z-amino)-5-fluorobenzoyl-Asp-fmk,
2-(Z-amino)-6-fluorobenzoyl-Asp-fmk,
cis-2-(Z-amino)-cyclohexanecarboxy-Asp-fmk,
2-(Z-amino)-5-methylbenzoyl-Asp-fmk,
2-(Z-amino)-6-methylbenzoyl-Asp-fmk,
2-(Z-amino)-6-chlorobenzoyl-Asp-fmk,
2-(Z-amino)-3-methoxybenzoyl-Asp-fmk,
3-(Z-amino)thiophene-2-carboxyl-Asp-fmk,
3-(methoxycarbonylamino)thiophene-2-carboxyl-Asp-fmk,
cis-2-(Z-amino)cyclopentanecarboxyl-Asp-fmk,
trans-2-(Z-amino)cyclopentanecarboxyl-Asp-fmk,
2-(Z-amino)benzoyl-Asp-DCB-methylketone,
methoxycarbonyl-Val-(2-aminobenzoyl)-Asp-fmk,
Z-Glu-(2-aminobenzoyl)-Asp-fmk, and
Z-Val-(2-aminobenzoyl)-Asp-fmk.

11. A pharmaceutical composition, comprising a compound of claim 1, and a pharmaceutically acceptable carrier.

12. A compound according to claim 1, wherein said compound has the Formula IV:

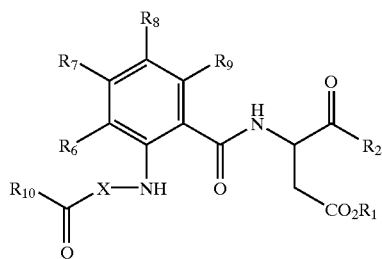

(IV)

or a pharmaceutically acceptable salt or prodrug thereof, wherein $R_2$ is hydrogen or optionally substituted alkyl, wherein the substituent is halo, hydroxy, alkoxy, aryloxy, alkylthio, arylthio, amino, acyloxy, or arylacyloxy; $R_6$–$R_9$ independently are hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, cyano, $C_1$–$C_6$ acylamino, hydroxy, $C_1$–$C_6$ acyloxy, $C_1$–$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle, selected from the group consisting of —OCH$_2$O—, —OCF$_2$O—, —CH$_2$)$_3$—, —CH$_2$)$_4$—, —OCH$_2$CH$_2$O—, —CH$_2$N(R$_{13}$)CH$_2$—, —CH$_2$CH$_2$N(R$_{13}$)CH$_2$—, —CH$_2$N(R$_{13}$)CH$_2$CH$_2$— and —CH=CH—CH=CH—; wherein $R_{13}$ is hydrogen, alkyl or cycloalkyl; $R_{10}$ is hydrogen, $C_1$–$C_6$ alkoxy, $C_1$–$C_6$ alkyl, $C_1$–$C_6$ haloalkyl, $C_6$–$C_{10}$ aryl, $C_4$–$C_7$ cycloalkyl, $C_6$–$C_{10}$ aryl($C_1$–$C_6$)alkyl, benzyloxy, substituted benzyloxy, or NR$_{11}$R$_{12}$; wherein $R_{11}$ and $R_{12}$ independently are hydrogen, $C_1$–$C_6$ alkyl, $C_1$–$C_6$ haloalkyl, $C_6$–$C_{10}$ aryl, $C_4$–$C_7$ cycloalkyl, $C_6$–$C_{10}$ aryl ($C_1$–$C_6$)alkyl, or $R_{11}$, and $R_{12}$ are combined to form a heterocyclic ring system selected from the group consisting of pyrrolidine, piperidine, piperazine, and morpholine.

13. A compound according to claim 12, wherein $R_2$ is hydrogen, fluoromethyl, acyloxymethyl, arylacyloxymethyl or aminomethyl.

14. A compound according to claim 12, wherein $R_{10}$ is benzyloxy.

15. A compound according to claim 12, wherein $R_1$ is H, Me or acetoxymethyl.

16. A compound according to claim 12, wherein X is a peptide of 1–2 amino acids or a bond.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens
<220> FEATURE:
<221> NAME/KEY: MOD_RES
<222> LOCATION: (1):(1)
<223> OTHER INFORMATION: N-terminal acetyl
<220> FEATURE:
<221> NAME/KEY: MOD_RES
<222> LOCATION: (4):(4)
<223> OTHER INFORMATION: C-terminal AMC (7-amino-4-methylcoumarin)

<400> SEQUENCE: 1

Asp Glu Val Asp
1